(12) United States Patent
Okada et al.

(10) Patent No.: US 8,758,897 B2
(45) Date of Patent: Jun. 24, 2014

(54) SCHIFF BASE TYPE COLOR CONVERSION LAYER, LIGHT ABSORBING LAYER, AND FILTER

(71) Applicant: Adeka Corporation, Tokyo (JP)

(72) Inventors: Mitsuhiro Okada, Tokyo (JP); Koichi Shigeno, Tokyo (JP)

(73) Assignee: Adeka Corporation, Tokyo (JP)

( * ) Notice: Subject to any disclaimer, the term of this patent is extended or adjusted under 35 U.S.C. 154(b) by 0 days.

(21) Appl. No.: 13/890,571

(22) Filed: May 9, 2013

(65) Prior Publication Data

US 2013/0252024 A1    Sep. 26, 2013

Related U.S. Application Data

(62) Division of application No. 13/055,937, filed as application No. PCT/JP2010/061153 on Jun. 30, 2010, now Pat. No. 8,568,884.

(30) Foreign Application Priority Data

Jul. 31, 2009   (JP) ................................. 2009-179089

(51) Int. Cl.
*B32B 27/20* (2006.01)
*H01J 1/62* (2006.01)

(52) U.S. Cl.
USPC .......................... 428/411.1; 428/913; 313/483

(58) Field of Classification Search
None
See application file for complete search history.

(56) References Cited

U.S. PATENT DOCUMENTS 7,408,072 B2   8/2008   Okada et al.
7,420,065 B2   9/2008   Okada et al.

FOREIGN PATENT DOCUMENTS

| JP | 2004-034645 | 2/2004 |
|---|---|---|
| JP | 2004-345212 | 12/2004 |
| JP | 2005-255992 | 9/2005 |
| JP | 2007-210890 | 8/2007 |
| JP | 2008-195749 | 8/2008 |
| WO | WO2004/072053 | 8/2004 |
| WO | WO2005/078024 | 8/2005 |

OTHER PUBLICATIONS

International Search Report—PCT/JP2010/061153—Jul. 27, 2010.
Registry (STN) [online], Mar. 8, 2007—[Jul. 13, 2010], CAS 925701-13-09.
Mitra et al—Mononuclear Schiff Base Boron Halides: Synthesis, Characterization, and Dealkylation of Trimethyl Phosphate, Inorganic Chemisty, 2006, 45(23), p. 9213-9224.
Singh et al.—Studies on Fluoroboron Derivatives of Azomethines, Indian Journal of Chemistry, Section A: Inorganic, Physical, Theoretical & Analytical, 1982, 21A (8), p. 833-834.
Tripathi et al.—Fluoroboron Derivatives of N-Substituted Salicyl Aldimenes, Inorganic and Nuclear Chemistry Letters, 1978, 14 (2/3), p. 97-99.

*Primary Examiner* — Ramsey Zacharia
(74) *Attorney, Agent, or Firm* — Young & Thompson

(57) ABSTRACT

Disclosed are a compound that emits fluorescence, particularly in its solid state, and is suited to provide a color converting material with various improved performance properties over prior art and a light emitter, a color conversion filter, a color conversion device, and a photoelectric device each containing the compound; particularly a Schiff base type compound of formula (I) and a coloring material, a color conversion layer, a light absorbing layer, a color conversion filter, a light absorbing filter, a color-converting light-emitting device, and a photoelectric device each containing the compound.

(I)

The definition of the symbols in formula (I) is the same as in the specification.

8 Claims, 1 Drawing Sheet

SCHIFF BASE TYPE COLOR CONVERSION LAYER, LIGHT ABSORBING LAYER, AND FILTER

CROSS REFERENCE TO RELATED APPLICATIONS

This application is a division of application Ser. No. 13/055,937 filed on Jan. 26, 2011, which is a National Stage of PCT/JP2010/061153 filed on Jun. 30, 2010, which claims foreign priority to Japanese application No. 2009-179089 filed on Jul. 31, 2009. The entire contents of each of the above applications are hereby incorporated by reference.

TECHNICAL FIELD

This invention generally relates to a novel Schiff base type compound. The invention also relates to a coloring material, a color conversion layer, a light absorbing layer, a color conversion filter, a light absorbing filter, a color converting light emitting device, and a photoelectric device each containing the Schiff base type compound. More particularly, it relates to a color conversion filter useful in applications to: display devices, such as liquid crystal displays, PDPs, and organic electro luminescent displays; display panels of image sensors, personal computers, word processors, audio equipment, video equipment, car navigation systems, phones, personal digital assistants, and industrial instruments; lighting equipment, such as fluorescent lamps, LEDs, and EL lamps; colorant lasers; copy protect systems; and photoelectric devices, such as solar cells. The invention also relates to an optical filter (color conversion filter) that allows for multicolor display with high definition, high brightness, high efficiency, and good productivity.

BACKGROUND ART

Materials that absorb energy to excite electrons and emit electromagnetic radiation as extra energy when the excited electrons return to the ground state exhibit wavelength conversion performance and have been used as a color (or wavelength) converting colorant in dye or pigment formulations, optical filters, and agricultural filters. In particular, organic compounds of such materials have been studied extensively because they have more easily controllable absorption and emission wavelengths than inorganic compounds. Among them, compounds that emit absorbed energy as fluorescence are called fluorescent colorants. Of the fluorescent colorants those emitting visible fluorescence are of high utility and have found application in displays, lighting equipment, such as fluorescent lamps, biological or medical markers, and so on.

Schiff base type compounds have been used in the form of their metal complexes as an optical recording material or an optical filter material as disclosed in patent documents 1 to 3 (see below). Fluorescence-emitting colorants are applicable to a high brightness, high efficiency color conversion filter. Inter alia, those emitting fluorescence in their solid state have been awaited in view of high practical utility. For example, patent documents 4 to 7 (see below) disclose compounds that emit fluorescence in their solid state. However, the colorants disclosed in the literature are not quite sufficient in terms of various performance requirements.

Patent document 1: JP 2004-034645A
Patent document 2: JP 2004-345212A
Patent document 3: JP 2007-210890A
Patent document 4: WO 2004/072053
Patent document 5: WO 2005/078024
Patent document 6: JP 2005-255992A
Patent document 7: JP 2008-195749

SUMMARY OF INVENTION

Problem to be Solved by the Invention

An object of the invention is to provide a novel compound that emits fluorescence, particularly in a solid state, and is suited for use as a color converting material showing improvements in various performance properties over prior art. Another object of the invention is to provide a light emitter, a color conversion filter, a color conversion device, and a photoelectric device each containing the novel compound.

Means for Solving the Problem

As a result of extensive studies, the present inventors have found that a Schiff base type compound having a specific structure has a high fluorescence intensity and emits fluorescence in its solid state. The above objects of the invention are accomplished by use of the Schiff base type compound.

Based on the above finding, the invention provides a novel Schiff base type compound represented by general formula (I):

[Chem. 1]

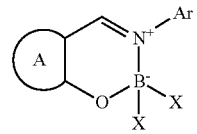

(I)

wherein ring A represents an aromatic ring, an aliphatic ring, or a heterocyclic ring; Ar represents a 5- or 6-membered heterocyclic or aromatic ring; and X represents a halogen atom, the aliphatic ring represented by ring A and the aromatic ring and the heterocyclic ring represented by ring A or Ar being optionally fused to a ring or optionally substituted.

The invention also provides a coloring material containing at least one Schiff base type compound of the invention.

The invention also provides a color conversion layer containing the coloring material of the invention.

The invention also provides a light absorbing layer containing the coloring material of the invention.

The invention also provides a color conversion filter including one or more color conversion layers at least one of which is the color conversion layer of the invention.

The invention also provides a light absorbing filter including one or more light absorbing layers at least one of which is the light absorbing layer of the invention.

The invention also provides a color-converting light-emitting device including a light emitting portion and one of the color conversion layer and the color conversion filter of the invention.

The invention also provides a photoelectric device including a photoelectric element and the color conversion filter of the invention.

Effect of the Invention

Having the above described structure, the invention provides a novel Schiff base type compound that emits fluorescence in its solid state suitable for use. Using a color conversion layer made of a coloring material containing the Schiff base type compound of the invention provides a color conversion filter, a color-converting light-emitting device, and a photoelectric device that achieve high brightness and high color conversion efficiency. Using a light absorbing layer made of the coloring material of the invention provides a light absorbing filter affording high color purity.

BRIEF DESCRIPTION OF THE ACCOMPANYING DRAWINGS

FIG. 1(a), FIG. 1(b), and FIG. 1(c) are each a schematic cross-section of a preferred embodiment of a light absorbing filter according to the invention.

BEST MODE FOR CARRYING OUT THE INVENTION

Figure 1:
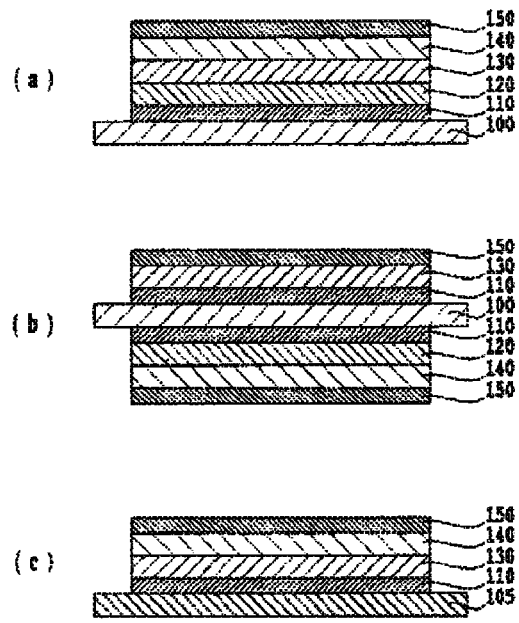

The Schiff base type compound of the invention and the coloring material, color conversion layer, light absorbing layer, color conversion filter, color-converting light-emitting device, and photoelectric device using the Schiff base type compound will be described in detail based on their preferred embodiments.

The Schiff base type compound of the invention is a compound represented by general formula (I) above and is characterized by having a 6-membered ring formed by the coordination of a boron atom and a nitrogen atom. It is excellent in fluorescence intensity and able to emit fluorescence in its solid state.

Examples of the aromatic ring represented by ring A and Ar in general formula (I) include benzene ring, naphthalene ring, anthracene ring, phenanthrene ring, pyrene ring, biphenyl ring, p-terphenyl ring, and m-terphenyl ring.

Examples of the aliphatic ring represented by ring A in general formula (I) include cyclopentane ring, cyclohexane ring, cycloheptane ring, and cyclooctane ring.

Examples of the heterocyclic ring represented by ring A and Ar in general formula (I) include pyrrole ring, thiophene ring, furan ring, pyran ring, thiopyran ring, imidazole ring, pyrazole ring, thiazole ring, isothiazole ring, oxazole ring, isoxazole ring, pyridine ring, pyrazine ring, pyrimidine ring, pyridazine ring, pyrrolidine ring, pyrazolidine ring, imidazolidine ring, isoxazolidine ring, isothiazolidine ring, piperidine ring, piperazine ring, morpholine ring, thiomorpholine ring, chromane ring, thiochromane ring, isochromane ring, isothiochromane ring, indoline ring, isoindoline ring, pyrindine ring, indolizine ring, indole ring, indazole ring, purine ring, quinolidine ring, isoquinoline ring, quinoline ring, naphthyridine ring, phthalazine ring, quinoxaline ring, quinazoline ring, cinnoline ring, pteridine ring, acridine ring, perimidine ring, phenanthroline ring, carbazole ring, carboline ring, phenazine ring, anthyridine ring, thiadiazole ring, oxadiazole ring, triazine ring, triazole ring, tetrazole ring, benzimidazole ring, benzoxazole ring, benzothiazole ring, benzothiadiazole ring, benzofuroxan ring, naphthoimidazole ring, benzotriazoles ring, and tetraazaindene ring.

Examples of the halogen atom represented by X in general formula (I) include fluorine, chloride, bromine, and iodine.

The aromatic ring and the heterocyclic ring represented by ring A and Ar and the aliphatic ring represented by ring A in general formula (I) may be substituted. Substituents include alkyl groups, such as methyl, ethyl, propyl, isopropyl, cyclopropyl, butyl, sec-butyl, tert-butyl, isobutyl, amyl, isoamyl, tert-amyl, cyclopentyl, hexyl, 2-hexyl, 3-hexyl, cyclohexyl, bicyclohexyl, 1-methylcyclohexyl, heptyl, 2-heptyl, 3-heptyl, isoheptyl, tert-heptyl, n-octyl, isooctyl, tert-octyl, 2-ethylhexyl, nonyl, isononyl, and decyl; alkoxy groups, such as methyloxy, ethyloxy, propyloxy, isopropyloxy, butyloxy, sec-butyloxy, tert-butyloxy, isobutyloxy, amyloxy, isoamyloxy, tert-amyloxy, hexyloxy, cyclohexyloxy, heptyloxy, isoheptyloxy, tert-heptyloxy, n-octyloxy, isooctyloxy, tert-octyloxy, 2-ethylhexyloxy, nonyloxy, and decyloxy; alkylthio groups, such as methylthio, ethylthio, propylthio, isopropylthio, butylthio, sec-butylthio, tert-butylthio, isobutylthio, amylthio, isoamylthio, tert-amylthio, hexylthio, cyclohexylthio, heptylthio, isoheptylthio, tert-heptylthio, n-octylthio, isooctylthio, tert-octylthio, and 2-ethylhexylthio; alkenyl groups, such as vinyl, 1-methylethenyl, 2-methylethenyl, 2-propenyl, 1-methyl-3-propenyl, 3-butenyl, 1-methyl-3-butenyl, isobutenyl, 3-pentenyl, 4-hexenyl, cyclohexenyl, bicyclohexenyl, heptenyl, octenyl, decenyl, pentadecenyl, eicosenyl, and tricosenyl; arylalkyl groups, such as benzyl, phenethyl, diphenylmethyl, triphenylmethyl, styryl, and cinnamyl; aryl groups, such as phenyl and naphthyl; aryloxy groups, such as phenoxy and naphthyloxy; arylthio groups, such as phenylthio and naphthylthio; heterocyclic groups, such as pyridyl, pyrimidyl, pyridazyl, piperidyl, pyranyl, pyrazolyl, triazyl, pyrrolyl, quinolyl, isoquinolyl, imidazolyl, benzimidazolyl, triazolyl, furyl, furanyl, benzofuranyl, thienyl, thiophenyl, benzothiophenyl, thiadiazolyl, thiazolyl, benzothiazolyl, oxazolyl, benzoxazolyl, isothiazolyl, isoxazolyl, indolyl, 2-pyrrolidinon-1-yl, 2-piperidon-1-yl, 2,4-dioxyimidazolidin-3-yl, and 2,4-dioxyoxazolidin-3-yl; halogen atoms, such as fluorine, chlorine, bromine, and iodine; acyl groups, such as acetyl, 2-chloroacetyl, propionyl, octanoyl, acryloyl, methacryloyl, phenylcarbonyl (i.e., benzoyl), phthaloyl, 4-trifluoromethylbenzoyl, pivaloyl, salicyloyl, oxaloyl, stearoyl, methoxycarbonyl, ethoxycarbonyl, t-butoxycarbonyl, n-octadecyloxycarbonyl, and carbamoyl; acyloxy groups, such as acetyloxy and benzoyloxy; an amino group; substituted amino groups, such as ethylamino, dimethylamino, diethylamino, butylamino, cyclopentylamino, 2-ethylhexylamino, dodecylamino, anilino, chlorophenylamino, toluidino, anisidino, N-methylanilino, diphenylamino, naphthylamino, 2-pyridylamino, methoxycarbonylamino, phenoxycarbonylamino, acetylamino, benzoylamino, formylamino, pivaloylamino, lauroylamino, carbamoylamino, N,N-dimethylaminocarbonylamino, N,N-diethylaminocarbonylamino, morpholinocarbonylamino, methoxycarbonylamino, ethoxycarbonylamino, t-butoxycarbonylamino, n-octadecyloxycarbonylamino, N-methylmethoxycarbonylamino, phenoxycarbonylamino, sulfamoylamino, N,N-dimethylaminosulfonylamino, methylsulfonylamino, butylsulfonylamino, and phenylsulfonylamino; sulfonamido, sulfonyl, carboxyl, cyano, sulfo, hydroxyl, nitro, mercapto, imido, carbamoyl, and sulfonamido. These substituents may be substituted. The substituted amino group, the carboxyl group, and the sulfo group may be in the form of a salt.

Of the Schiff base type compounds of general formula (I) those represented by general formula (II) shown below, particularly those represented by general formula (III) shown below are preferred; for they are prepared from easily available materials and exhibit more suitable fluorescence characteristics for use as a fluorescent material.

Of the Schiff base type compounds described, the following compounds are more preferred for their excellent fluorescence characteristics.

Compounds of general formula (II) or (III) in which $R^1$, $R^2$, $R^3$, and $R^4$ are each hydrogen, optionally substituted C1-C10 alkyl, or —NRR' (wherein R and R' are each C1-C10 alkyl and may be taken together with the adjacent $R^1$, $R^2$, $R^3$, or $R^4$ to form a ring structure) and/or Ar is a optionally substituted C6-C30 aromatic ring or a optionally substituted C3-C20 heterocyclic ring. The substituent on the aromatic or the heterocyclic ring represented by Ar is preferably selected from halogen, halogen-substituted C1-C5 alkyl, and/or —NRR' (wherein R and R' are each C1-C10 alkyl or C6-C10 aryl).

In particularly, compounds of general formula (II) or (III) in which $R^1$, $R^2$, $R^3$, and $R^4$ are each hydrogen, optionally substituted C1-C5 alkyl, or —NRR' (wherein R and R' are each C1-C5 alkyl and may be taken together with the adjacent $R^1$, $R^2$, $R^3$, or $R^4$ to form a ring structure) and/or Ar is a optionally substituted C6-C20 aromatic ring or a optionally substituted C3-C15 heterocyclic ring. The substituent on the aromatic or the heterocyclic ring represented by Ar is preferably halogen, halogen-substituted C1-C5 alkyl, and/or —NRR' (wherein R and R' are each C1-C5 alkyl or C6-C10 aryl).

Of the Schiff base type compounds described, the following compounds are also more preferred for their excellent light resistance.

Compounds of general formula (I) in which at least one of the hydrogen atoms bonded to ring A or Ar is displaced by an amino group represented by —NRR' (wherein R and R' each represent C1-C10 alkyl or C6-C10 aryl and may be each taken together with ring A or Ar to form a ring structure).

Compounds of general formula (II) or (III) in which at least one of the hydrogen atoms possessed by Ar, or $R^1$, $R^2$, $R^3$, or $R^4$ is displaced by an amino group represented by —NRR' (wherein R and R' each represent C1-C10 alkyl or C6-C10 aryl and may be each taken together with ring A or Ar to form a ring structure).

[Chem. 2]

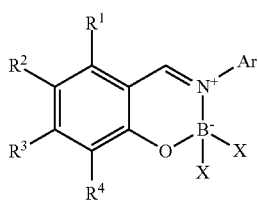

(II)

wherein $R^1$, $R^2$, $R^3$, and $R^4$ each independently represent a hydrogen atom, a halogen atom, a nitro group, a cyano group, a hydroxyl group, a carboxyl group, —NRR', an optionally substituted alkyl group having 1 to 20 carbon atoms, an optionally substituted aryl group having 6 to 20 carbon atoms, an optionally substituted heterocyclic ring having 4 to 20 carbon atoms, or an optionally substituted arylalkyl group having 7 to 20 carbon atoms; or adjacent two of $R^1$, $R^2$, $R^3$, and $R^4$ are taken together to form an aliphatic, aromatic, or heterocyclic ring, the methylene chain of the alkyl group or the arylalkyl group and the bond between the aryl group and the benzene ring being optionally interrupted by —O—, —S—, —SO$_2$—, —CO—, —COO—, or —COO—; and R and R' each represent an alkyl group having 1 to 20 carbon atoms or an aryl group having 6 to 20 carbon atoms; or R and R' are taken together with the adjacent $R^1$, $R^2$, $R^3$, or $R^4$ to form a ring structure, the aromatic ring formed by the connection of adjacent two of $R^1$, $R^2$, $R^3$, and $R^4$ being optionally fused to a ring or substituted; Ar and X are as defined for general formula (I).

[Chem. 3]

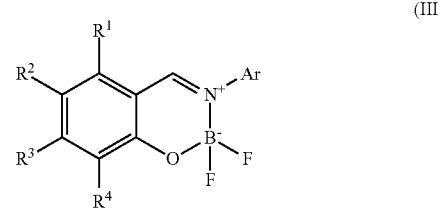

(III)

wherein Ar is as defined for general formula (I); and $R^1$, $R^2$, $R^3$, and $R^4$ are as defined for general formula (II).

The optionally substituted alkyl group having 1 to 20 carbon atoms represented by $R^1$, $R^2$, $R^3$, and $R^4$ in general formulae (II) and (III) may be straight chain, branched, or cyclic. Examples thereof include methyl, ethyl, propyl, isopropyl, butyl, s-butyl, t-butyl, isobutyl, amyl, isoamyl, t-amyl, hexyl, heptyl, isoheptyl, t-heptyl, n-octyl, isooctyl, t-octyl, 2-ethylhexyl, n-nonyl, n-decyl, n-dodecyl, n-tridecyl, n-tetradecyl, n-pentadecyl, n-hexadecyl, n-heptadecyl, n-octadecyl, cyclopropyl, cyclobutyl, cyclopentyl, cyclohexyl, cycloheptyl, cyclooctyl, cyclononyl, and cyclodecyl. Examples of the alkyl group the methylene chain of which is interrupted by —O— include methoxy, ethoxy, propyloxy, isopropyloxy, methoxymethyl, ethoxymethyl, and 2-methoxyethyl. Examples of the alkyl group the methylene chain of which is interrupted by —S— include methylthio, ethylthio, butylthio, and pentylthio. Examples of the alkyl group the methylene chain of which is interrupted by —SO$_2$— include methylsulfonyl, ethylsulfonyl, butylsulfonyl, and pentylsulfonyl. Examples of the alkyl group the methylene chain of which is interrupted by —CO— include acetyl, 1-carbonylethyl, acetylmethyl, 1-carbonylpropyl, 2-oxobutyl, 2-acetylethyl, 1-carbonylisopropyl, and cyclopentanecarbonyl. Examples of the alkyl group the methylene chain of which is interrupted by —COO— include acetoxy, propionyloxy, and butyryloxy. Examples of the alkyl group the methylene chain of which is interrupted by —COO— include methoxycarbonyl, ethoxycarbonyl, and isopropyloxycarbonyl.

Examples of the optionally substituted aryl group having 6 to 20 carbon atoms represented by $R^1$, $R^2$, $R^3$, and $R^4$ in general formulae (II) and (III) include phenyl, naphthyl, and biphenyl. Examples of the aryl group of which the bond to the benzene ring is interrupted by —O— include phenoxy, 1-naphthoxy, and 2-naphthoxy. Examples of the aryl group of which the bond to the benzene ring is interrupted by —S— include phenylthio, 1-naphthylthio, and 2-naphthylthio. Examples of the aryl group of which the bond to the benzene ring is interrupted by —SO$_2$— include phenylsulfone, 1-naphthylsulfone, and 2-naphthylsulfone. Examples of the aryl group of which the bond to the benzene ring is interrupted by —CO— include benzoyl, 1-naphthoyl, and 2-naphthoyl. Examples of the aryl group of which the bond to the benzene ring is interrupted by —COO— include benzoyloxy, 1-naphthoyloxy, and 2-naphthoyloxy. Examples of the aryl group of which the bond to the benzene ring is interrupted by —COO— include phenoxycarbonyl and 1-naphthoxycarbonyl.

Examples of the optionally substituted heterocyclic ring having 4 to 20 carbon atoms represented by $R^1$, $R^2$, $R^3$, and $R^4$ in general formulae (II) and (III) include pyrrolyl, pyridyl, pyrimidyl, pyridazyl, piperazyl, piperidyl, pyranyl, pyrazolyl, triazyl, pyrrolidyl, quinolyl, isoquinolyl, imidazolyl, benzimidazolyl, triazolyl, furyl, furanyl, benzofuranyl, thienyl, thiophenyl, benzothiophenyl, thiadiazolyl, thiazolyl, benzothiazolyl, oxazolyl, benzoxazolyl, isothiazolyl, isoxazolyl, indolyl, julolidyl, morpholinyl, thiomorpholinyl, 2-pyrrolidinon-1-yl, 2-piperidon-1-yl, 2,4-dioxyimidazolidin-3-yl, and 2,4-dioxyoxazolidin-3-yl.

Examples of the optionally substituted arylalkyl group having 7 to 20 carbon atoms represented by $R^1$, $R^2$, $R^3$, and $R^4$ in general formulae (II) and (III) include benzyl, phenethyl, 2-phenylpropyl, diphenylmethyl, triphenylmethyl, and 4-chlorophenylmethyl. Examples of the arylalkyl group the methylene chain of which is interrupted by —O— include benzyloxy, phenoxymethyl, phenoxyethyl, 1-naphthylmethoxy, 2-naphthylmethoxy, and 1-anthrylmethoxy. Examples of the arylalkyl group the methylene chain of which is interrupted by —S— include benzylthio, phenylthiomethyl, and phenylthioethyl. Examples of the arylalkyl group the methylene chain of which is interrupted by —SO$_2$— is exemplified by benzylsulfonyl. Examples of the arylalkyl group the methylene chain of which is interrupted by —CO— include benzylcarbonyl, phenethylcarbonyl, and 1-naphthylmethylcarbonyl. Examples of the arylalkyl group the methylene chain of which is interrupted by —COO— include a phenylacetate group and a 1-naphthylacetate group. Examples of the arylalkyl group the methylene chain of which is interrupted by —COO— include benzyloxycarbonyl and phenethyloxycarbonyl.

Adjacent two of $R^1$, $R^2$, $R^3$, and $R^4$ in general formulae (II) and (III) may be taken together to form a cyclic structure. Examples of such a cyclic structure include benzene ring, cyclopentane ring, cyclohexane ring, cycloheptane ring, cyclooctane ring, imidazole ring, thiazole ring, pyrazole ring, oxazole ring, isoxazole ring, thiophene ring, furan ring, pyrrole ring, pyridine ring, piperazine ring, piperidine ring, morpholine ring, pyrazine ring, pyrone ring, and pyrrolidine ring. These cyclic structure may be substituted.

Examples of the alkyl group having 1 to 20 carbon atoms and the aryl group having 6 to 20 carbon atoms represented by R and R' and the cyclic structure formed by R or R' and the adjacent $R^1$, $R^2$, $R^3$, or $R^4$ in general formulae (II) and (III) are the same as listed with respect to general formula (I).

Examples of the substituents of the alkyl group having 1 to 20 carbon atoms, the aryl group having 6 to 20 carbon atoms, the heterocyclic ring having 4 to 20 carbon atoms, and the arylalkyl group having 7 to 20 carbon atoms in general formulae (II) and (III) are the same as those listed as substituents with respect to general formula (I). When the substituent of the alkyl, aryl, or arylalkyl as $R^1$, $R^2$, $R^3$, or $R^4$ contains a carbon atom, the total number of carbon atoms inclusive of that of the substituent shall fall within the respective ranges recited.

Specific examples of the Schiff base type compounds of general formulae (I) to (III) include, but are not limited to, the following compounds numbered 1 through 56.

[Chem. 4]

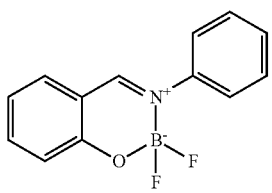

Compound No. 1

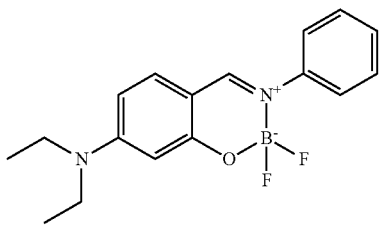

Compound No. 2

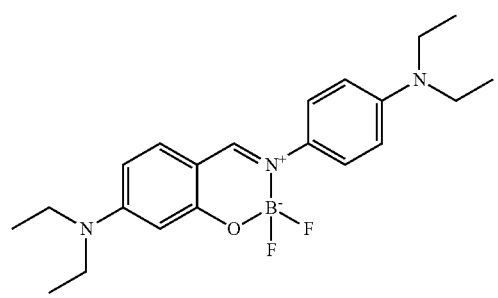

Compound No. 3

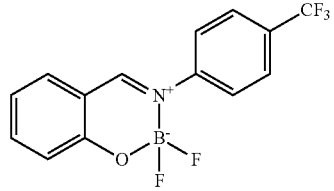

Compound No. 4

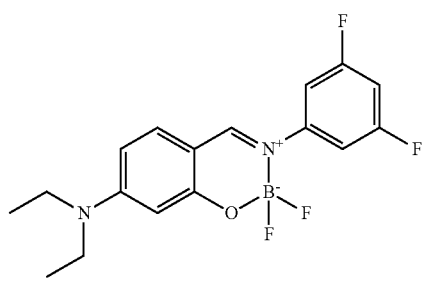

Compound No. 5

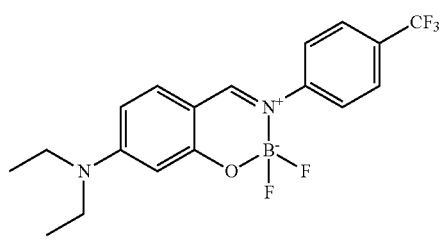

Compound No. 6

-continued
Compound No. 7
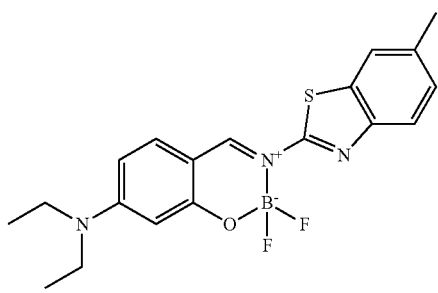
Compound No. 12
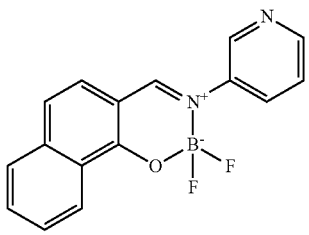
[Chem. 5]
Compound No. 8
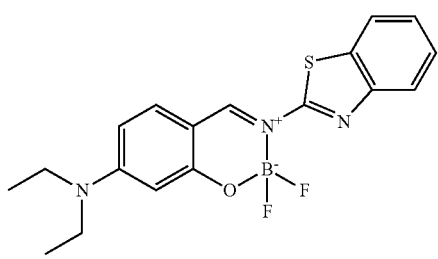
Compound No. 13
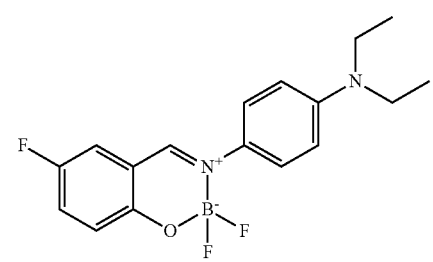
Compound No. 9
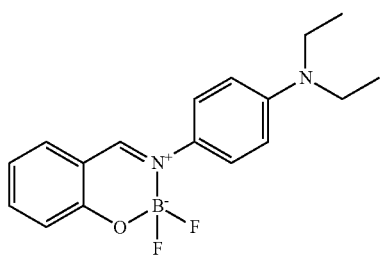
Compound No. 14
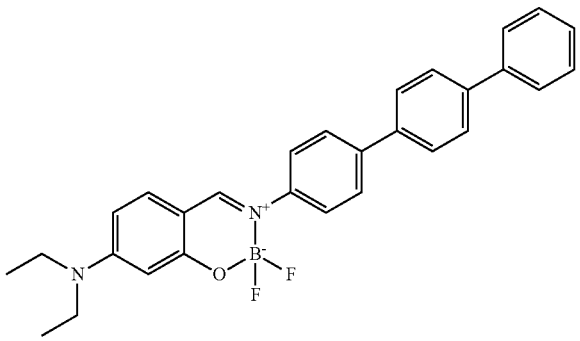
Compound No. 10
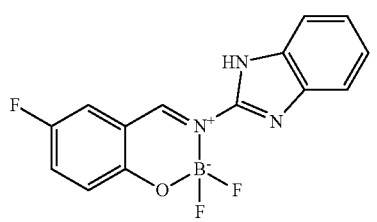
Compound No. 15
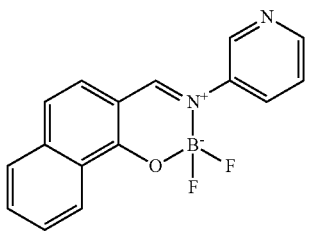
Compound No. 11
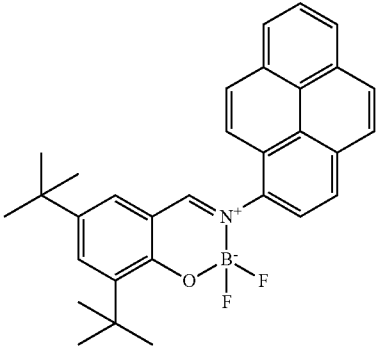
Compound No. 16
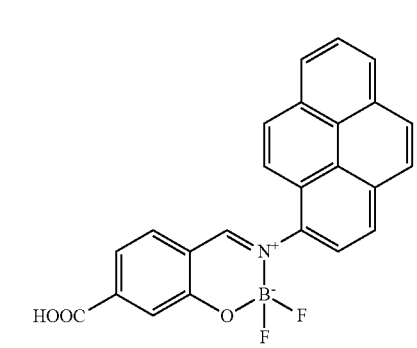

Compound No. 17
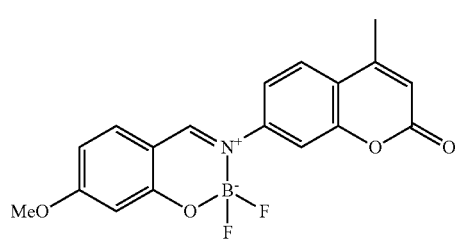
Compound No. 18
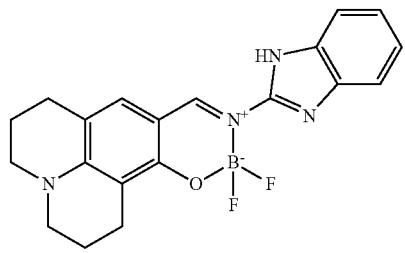
Compound No. 19
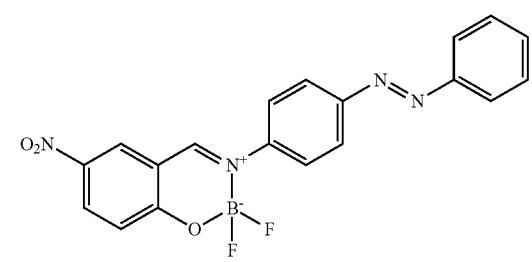
Compound No. 20
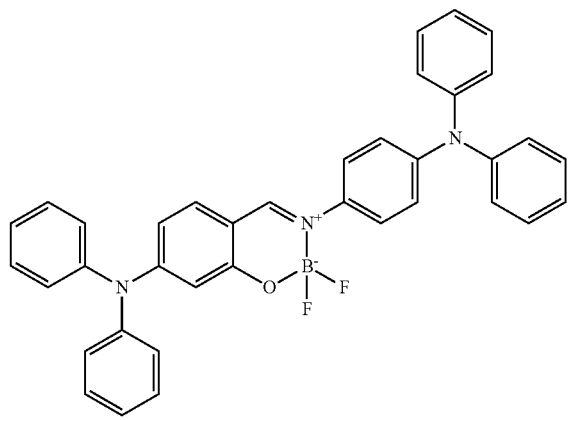
Compound No. 21
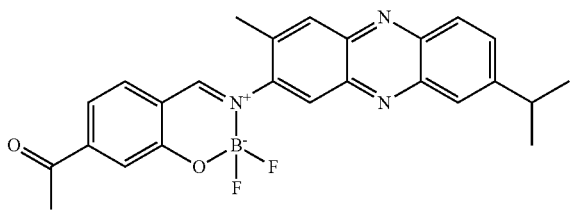
Compound No. 22
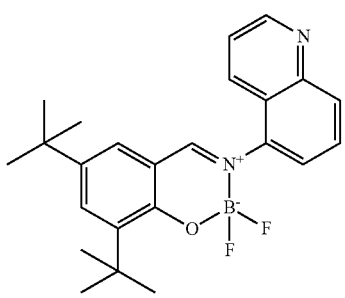
Compound No. 23
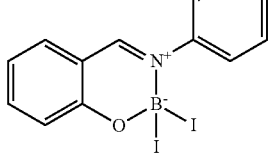
[Chem. 6]
Compound No. 24
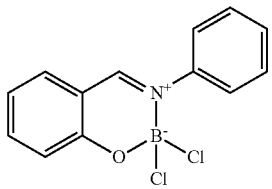
Compound No. 25
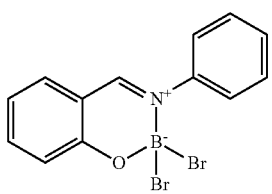
Compound No. 26
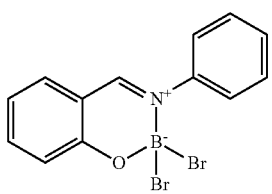
Compound No. 27
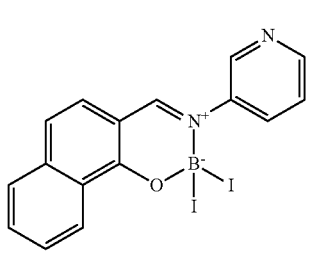

-continued
Compound No. 28
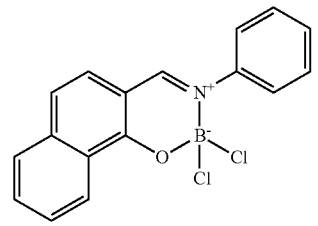
Compound No. 29
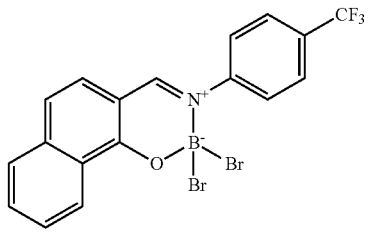
Compound No. 30
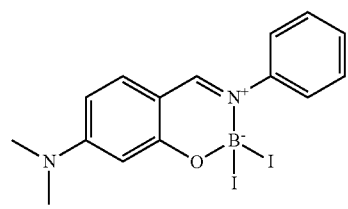
Compound No. 31
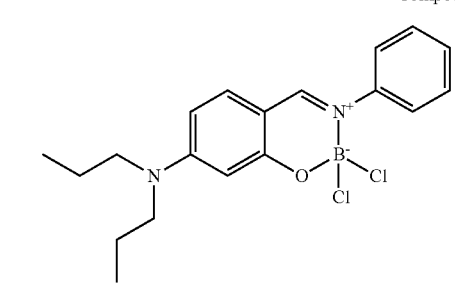
Compound No. 32
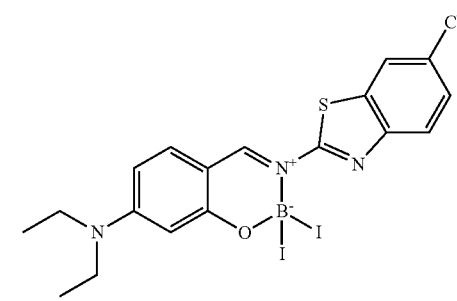
Compound No. 33
Compound No. 34
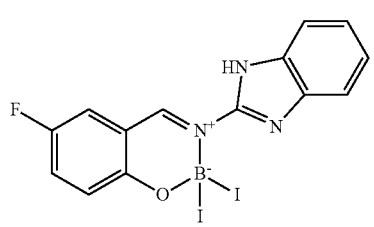
Compound No. 35
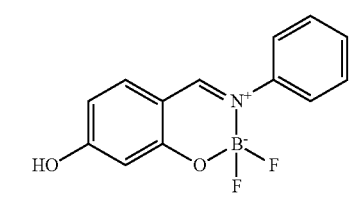
Compound No. 36
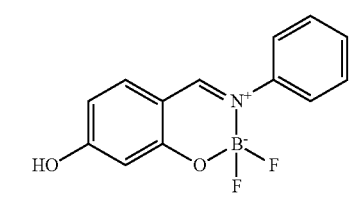
Compound No. 37
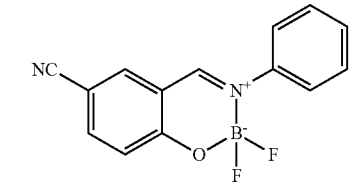
Compound No. 38
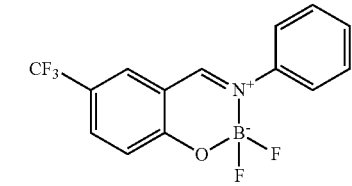
Compound No. 39
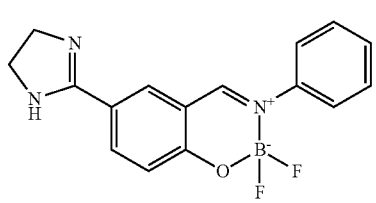
Compound No. 40
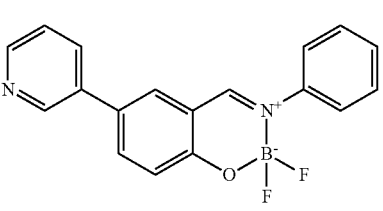

Compound No. 41
Compound No. 42
Compound No. 43
Compound No. 44
Compound No. 45

[Chem. 7]

Compound No. 46
Compound No. 47
Compound No. 48
Compound No. 49
Compound No. 50

-continued

Compound No.51

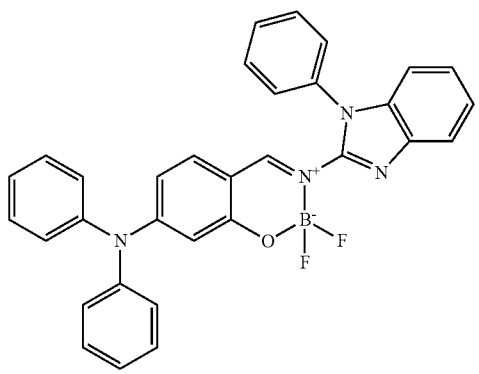

[Chem. 8]

Compound No.52

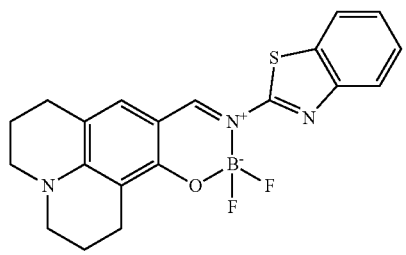

Compound No.53

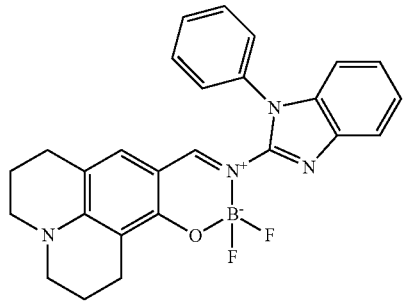

Compound No.54

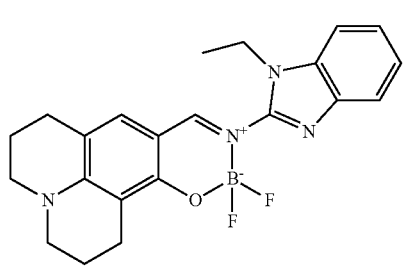

Compound No.55

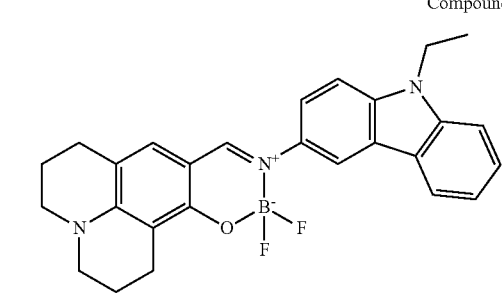

-continued

Compound No. 56

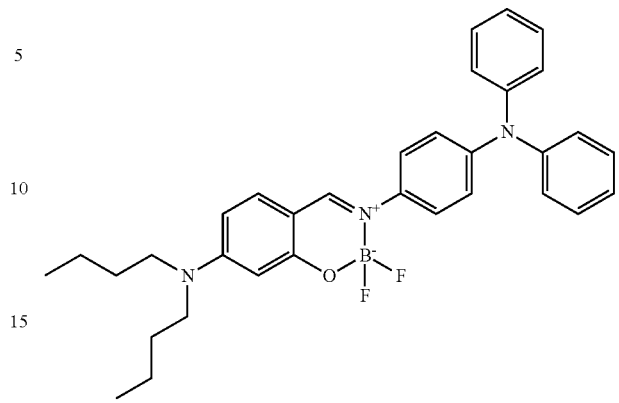

The Schiff base type compound of general formula (I) is not limited by the process of preparation and can be obtained by any processes making use of well-known reactions. For example, the compound may be synthesized by the reaction between a corresponding aldehyde compound and a corresponding amine compound as illustrated in the reaction scheme of [Chem. 9] below.

[Chem. 9]

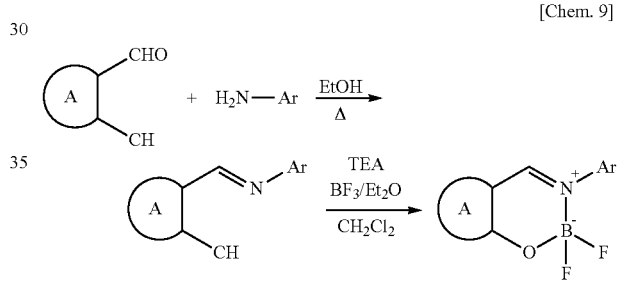

wherein ring A represents an aromatic ring, an aliphatic ring, or a heterocyclic ring; Ar represents a 5- or 6-membered heterocyclic or aromatic ring: the aliphatic ring represented by ring A and the aromatic ring and the heterocyclic ring represented by ring A or Ar being optionally fused to a ring or optionally substituted.

The Schiff base type compound of the invention is suitable for use as a colorant absorbing light of from 300 nm to 700 nm. It is useful, for example, as a colorant in an optical recording layer of DVD-Rs; a colorant for optical filters used in image displays, such as liquid crystal displays (LCDs), plasma display panels (PDPs), electro luminescence displays (ELDs), cathode ray tube displays (CRTs), fluorescent display tubes, and field emission displays; a light-emitting colorant for organic electro luminescence; a color toner, an inkjet ink, a colorant for coatings, an LED lamp, and an electro luminescence lamp. The Schiff base type compound of the invention may also be used as a spectral sensitizer for photoelectric devices or silver salt photographic materials or a sensitizer for optical reactions.

The Schiff base type compound of the invention may be incorporated into the light emitting portion of the image display devices. For instance, in application to an EL device including an anode, a cathode, and a plurality of layers between the anode and the cathode, the Schiff base type compound is incorporated into at least one of the layers. The Schiff base type compound may be incorporated into the photoelectric device. For instance, the compound may be adsorbed onto the surface of a semiconductor, e.g., titanium oxide or zinc oxide, to generate electricity.

The Schiff base type compound of the invention converts light of 300 to 700 nm to fluorescence of 400 to 750 nm and is therefore useful as a fluorescent material. The Schiff base type compound of the invention emits fluorescence even in its solid state and converts light of 350 to 650 nm to fluorescence of 400 to 750 nm and is therefore useful as a fluorescent pigment.

The coloring material of the invention contains at least one Schiff base type compound of the invention and, where needed, may further contain other colorants than the Schiff base type compound of the invention. The coloring material is a composition especially necessary for the preparation of a color conversion layer or a light absorbing layer. The form of the coloring material is not particularly limited and may be a coating liquid, a filler, a sealant, an adhesive, or the like form.

The Schiff base type compound content in the coloring material designed for making a color conversion layer is preferably 0.001% to 50% by mass, more preferably 0.01% to 20% by mass, based on the solids content (i.e., non-solvent content). The Schiff base type compound content in the coloring material designed for making a light absorbing layer is preferably 0.001% to 50% by mass, more preferably 0.01% to 20% by mass, based on the solids content.

If desired, the coloring material of the invention may contain a binder (e.g., a photocuring resin, a thermosetting resin, or a thermoplastic resin), a photo stabilizer, a curing agent, an IR absorber, a UV absorber, an antioxidant, a surfactant, an antistatic agent, a flame retarder, a lubricant, a heavy metal deactivator, hydrotalcite, an organic carboxylic acid, a coloring agent, a processing aid, inorganic additives, a filler, a clarifier, a nucleating agent, a crystallizing agent, a quencher, a solvent, and so forth. Of the Schiff base type compounds of the invention those which emit fluorescence will be made usable in the coloring material designed for making a color conversion layer by adding a quencher to the coloring material.

The other colorants that may be used in combination are not particularly limited and include, for example, cyanine colorants, pyridine colorants, oxazine colorants, coumarin colorants, coumarin dyes, naphthalimide colorants, pyromethene colorants, perylene colorants, pyrene colorants, anthracene colorants, styryl colorants, rhodamine colorants, azo colorants, quinone colorants, squarylium colorants, diketopyrrolopyrrole colorants, iridium complex colorants, and europium complex colorants. The content of the other colorants in the coloring material of the invention is preferably 0.1 to 50 parts by mass per 100 parts by mass of the Schiff base type compound of the invention.

Examples of the quencher include, but are not limited to, aminium colorants, iminium colorants, cyanine colorants, and transition metal chelate compounds. The content of the quencher in the coloring material of the invention is preferably 1 to 5000 parts by mass, more preferably 10 to 1000 parts by mass, per 100 parts by mass of the Schiff base type compound.

Examples of the solvent include, but are not limited to, water, alcohols, diols, ketones, esters, ethers, aliphatic or alicyclic hydrocarbons, aromatic hydrocarbons, cyano-containing hydrocarbons, and halogenated aromatic hydrocarbons.

The color conversion layer according to the invention contains the coloring material of the invention and has the characteristic of absorbing light and emitting light as fluorescence having a longer wavelength than that of the light absorbed. The form of the color conversion layer is not particularly limited and may be, for example, film or pellets.

More specifically, the color conversion layer of the invention may be a single layer of the Schiff base type compound alone or in admixture with other colorant(s) formed on a substrate or a laminate composed of such a layer and other layer(s) formed on a substrate.

The single layer or the laminate is prepared by forming a coating layer on a permanent or temporary substrate by, for example, evaporation deposition, sputtering, solution processes using a solution or a dispersion, such as dip coating, air knife coating, curtain coating, roller coating, wire bar coating, gravure coating, and spin coating, or extrusion.

The color conversion layer of the invention may be a film or a filter prepared from a mixture of the Schiff base type compound dissolved or dispersed in a binder resin.

The film or filter is prepared by applying a mixture of the Schiff base type compound dissolved or dispersed in a binder resin to a permanent or temporary substrate by the same method as described for the preparation of a single layer or a laminate. The film can be a self-supporting film, which is obtained by forming the film on a temporary substrate by the above described method and peeling the film from the temporary substrate.

Examples of the binder resin include natural polymeric materials, such as gelatin, casein, starch, cellulose derivatives, and alginic acid; synthetic polymers, such as polymethyl methacrylate, polyvinyl butyral, polyvinylpyrrolidone, polyvinyl alcohol, polyvinyl chloride, styrene-butadiene copolymers, polystyrene, polycarbonate, polyamide, ethylene-vinyl acetate copolymer resins, polyfluorene reins, and silicone resins; and adhesives of rubber, acrylic or silicone type.

The solvent is not particularly limited, and examples of suitable solvents include those described with reference to the coloring material of the invention.

A self-supporting film can also be directly molded from a mixture of the Schiff base type compound of the invention and a polymer by extrusion, casting, or calendering. Examples of useful polymers include cellulose esters, such as diacetyl cellulose, triacetyl cellulose (TAC), propionyl cellulose, butyryl cellulose, acetylpropionyl cellulose, and nitrocellulose; polyamides; polycarbonates; polyesters, such as polyethylene terephthalate, polyethylene naphthalate, polybutylene terephthalate, poly-1,4-cyclohexanedimethylene terephthalate, polyethylene-1,2-diphenoxyethane 4,4'-dicargoxylate, and polybutylene terephthalate; polystyrene; polyolefins, such as polyethylene, polypropylene, and polymethylpentene; acrylic resins, such as polymethyl methacrylate; polysulfone; polyether sulfone; polyether ketone; polyether imide; polyoxyethylene; and norbornene resins.

The color conversion layer may also be prepared by mixing the Schiff base type compound of the invention with a photocuring resin and/or thermosetting resin and a photopolymerization initiator and/or a thermal curing agent and applying light and/or heat to form a cured film.

In the case where the color conversion layer of the invention is for applications involving patterning by wet etching, it is preferred for the color conversion layer to contain the Schiff base type compound of formulae (I), (II) or (III) and a photocuring or photo- and thermal-curing resin (i.e., resist). A cured product of the photocuring or photo- and thermal-curing resin (resist) functions as a binder of the color conversion film after patterning. To facilitate smooth patterning, the photocuring or photo- and thermal-curing resin is desirably soluble in an organic solvent or an alkali solution in an unexposed state. Examples of useful photocuring or photo- and thermal-curing resin (resist) include (1) a composition containing a polyfunctional acrylic monomer and oligomer having at least two acryloyl or methacryloyl groups and a photo- or thermal polymerization initiator, (2) a composition containing a polyvinyl succinate and a sensitizer, (3) a composition containing an acyclic or cyclic olefin and a bisazide (nitrene is generated to crosslink the olefin), and (4) a composition containing an epoxy-containing monomer and an acid generator. The composition (1) that contains a polyfunctional acrylic monomer and oligomer and a photo- or thermal polymerization initiator is particularly preferred; for it is capable of high definition patterning and, after polymerization and cure, provides high reliability in terms of, e.g., solvent resistance and heat resistance.

The light absorbing layer according to the invention is made of the coloring material of the invention and has the characteristic of absorbing light in the visible region. The light absorbing layer of the invention may be in any form such as those described with reference to the color conversion layer.

The color conversion filter according to the invention includes one or more color conversion layers at least one of which contains the Schiff base type compound of the invention. The color conversion filter of the invention is applicable to devices having a light emitting portion. When applied to, for example, an organic electro luminescence displays, the color conversion filter converts light from a device emitting monochromatic light in the region between near ultraviolet and blue to blue, green, or red light only in necessary regions of the device thereby to achieve full color display. When applied to organic EL lamps or LED lamps, the color conversion filter converts the whole or part of near ultraviolet to blue light to light of longer wavelengths to obtain white light. In applications to liquid crystal displays, the color conversion filter may be incorporated into a polarizer, a light guide panel, or a diffuser, disposed between optical films, or disposed as a laminate with another color conversion layer, so that the light incident to be absorbed by a color conversion filter is previously converted to effective light, thereby to improve brightness and save the power.

Capable of making a desired color, the color conversion filter of the invention is also useful in LED lamps, colorant lasers, and the like. The color conversion filter is also applicable to devices having a photoelectric element. When applied to, for example, a solar cell, it is capable of absorbing light of wavelengths with which the photoelectric element achieves only low photovoltaic efficiency and converting it to light of wavelengths with which the photoelectric element achieves high photovoltaic efficiency.

The light absorbing filter according to the invention includes one or more light absorbing layers at least one of which contains the Schiff base type compound of the invention. The light absorbing filter of the invention is used as an optical element of an optical filter for image display devices, such as liquid crystal displays (LCDs), plasma display panels (PDPs), electro luminescence displays (ELDs), cathode ray tube displays (CRTs), fluorescent display tubes, and field emission displays.

Configurations of preferred embodiments of the light absorbing filter of the invention are illustrated in FIGS. 1(a), 1(b), and 1(c). The light absorbing filter may include a substrate 100 and an optically functional layer 120 containing the Schiff base type compound of the invention and may optionally include, when needed, a primer layer 110, an antireflective layer 130, a hardcoat layer 140 and/or a lubricating layer 150. As illustrated in FIG. 1(a), a primer layer 110, an optically functional layer 120, an antireflective layer 130, a hardcoat layer 140, and a lubricating layer 150 may be stacked in that order on one side of a substrate 100. As illustrated in FIG. 1(b), a primer layer 110, an optically functional layer 120, a hardcoat layer 140 and a lubricating layer 150 may be stacked in that order on one side of a substrate 100, and a primer layer 110, an antireflective layer 130, and a lubricating layer 150 may be stacked in that order on the other side of the substrate 100. As illustrated in FIG. 1(c), a primer layer 110, an antireflective layer 130, a hardcoat layer 140, and a lubricating layer 150 may be stacked in that order on one side of an optically functional substrate 105 containing the Schiff base type compound of the invention.

The substrate 100 may be of an inorganic material such as glass or a polymer such as illustrated above with reference to the color conversion layer. The substrate 100 preferably has a visible light transmittance of at least 80%, more preferably 86% or more; a haze of 2% or less, more preferably 1% or less; and a refractive index of 1.45 to 1.70. The thickness of the substrate 100 is decided as appropriate to the intended use and the like and is generally preferably, but not limited to, from 10 to 10000 μm.

The optically functional substrate 105 used in the configuration of FIG. 1(c) may be the above-described self-supporting light absorbing layer of the invention. The optically functional substrate 105 preferably has a haze of 2% or less, more preferably 1% or less, and a refractive index of 1.45 to 1.70. The thickness of the optically functional substrate 105 is decided as appropriate to the intended use and the like and is generally preferably, but not limited to, from 10 to 10000 μm.

The substrate 100 and the optically functional substrate 105 may contain an IR absorber, a UV absorber, inorganic particles, and the like. The substrate 100 and the optically functional substrate 105 may be subjected to a surface treatment, such as chemical treatment, mechanical treatment, corona discharge treatment, flame treatment, UV irradiation, high frequency treatment, glow discharge treatment, active plasma treatment, laser treatment, mixed acid treatment, and ozone oxidation.

The primer layer 110 is provided to enhance the adhesion between the substrate 100 or the optically functional substrate 105 (these substrates will sometimes be referred inclusively to "substrate") and an adjoining layer, e.g., the optically functional layer 120 and/or the antireflective layer 130. The primer layer 110 may be a layer of a polymer having a glass transition temperature of −60° to 60° C., a layer with a rough surface on its side opposite to the substrate, or a layer containing a polymer having affinity for both the substrate and the adjoining layer. The primer layer 110 may be provided to improve the affinity between an adhesive for attaching the light absorbing filter to a display (light source) and the light absorbing filter. The thickness of the primer layer is preferably 2 nm to 20 μm, more preferably 5 nm to 5 μm, even more preferably 20 nm to 2 μm, still more preferably 50 nm to 1 μm, and most preferably 80 nm to 300 nm.

The primer layer 110 containing a polymer with a glass transition temperature of −60° to 60° C. bonds the substrate and the adjoining layer by its own tackiness. The polymer having a glass transition temperature of −60° to 60° C. is obtained by homo- or copolymerization of vinyl chloride, vinylidene chloride, vinyl acetate, butadiene, neoprene, styrene, chloroprene, an acrylic ester, a methacrylic ester, acrylonitrile, or methyl vinyl ether. The glass transition temperature of the polymer is preferably −60° to 50° C., more preferably −60° to 40° C., even more preferably −60° to 30° C., still more preferably −60° to 25° C., and most preferably −60° to 20° C. The primer layer preferably has an elastic modulus at 25° C. of 1 to 1000 MPa, more preferably 5 to 800 MPa, even more preferably 10 to 500 MPa.

The primer layer 110 that has a rough surface on its side opposite to the substrate bonds the substrate and the adjoining layer by the mechanical action of its surface roughness. The primer layer 110 with a rough surface is formed easily by application of a polymer latex. The latex preferably has an average particle size of 0.02 to 3 μm, more preferably 0.05 to 1 μm.

The primer layer 110 may also be a layer of a polymer having affinity for the binder polymer of the adjoining layer. It is preferred for the polymer to have affinity for the substrate as well. Examples of a polymer with affinity for the binder polymer of, e.g., the optically functional layer 120 include acrylic resins, cellulose derivatives, gelatin, casein, starch, polyvinyl alcohol, soluble nylon, and polymer lattices. Two or more primer layers 110 may be provided. The primer layer 110 may contain a solvent that swells the substrate 100, a matting agent, a surfactant, an antistatic agent, a coating aid, a hardening agent, and so forth.

The optically functional layer 120 may be formed of the light absorbing layer of the invention. The optically functional layer 120 is provided on the substrate 100 or the primer layer 110 formed on the substrate 100. The optically functional layer 120 may be formed by bonding a self-supporting film to the primer layer 110 or the substrate 100. The thickness of the optically function layer 120 is decided as appropriate to the intended use and the like and is generally preferably, but not limited to, from 0.1 to 100 μm.

Containing the Schiff base type compound of the invention, the optically functional layer 120 or the optically functional substrate 105 can be designed to function as a light absorbing layer that absorbs light in the wavelength range of from 400 nm to 700 nm. In this case, the optically functional layer 120 preferably contains a quencher in order to quench the fluorescence generated by the Schiff base type compound on absorbing light of the wavelength range recited. The quenchers previously described with reference to the coloring material may be used. This light absorbing layer may be designed to have a desired hue by adding, to the optically functional layer 120, a colorant absorbing light of other wavelengths, which is selected from the compounds described above as other colorants with respect to the coloring material.

In the cases where the optically functional layer 120 is designed to function as a light absorbing layer, the amount of the Schiff base type compound of the invention to be used is suitably 1 to 1000 mg, preferably 5 to 300 mg, per square meter of the light absorbing filter. With the recited amount of the Schiff base type compound, the optically functional layer 120 exhibits a sufficient light absorbing effect as well as a suitable optical density to provide good display quality and brightness. In the case where the optically functional substrate 105 as in the configuration of FIG. 1(c) is used as a light absorbing layer, too, the Schiff base type compound of the invention is preferably used in an amount falling within the recited range.

The antireflective layer 130 is provided to prevent reflection on the light absorbing filter of the invention to improve the transmittance. The antireflective layer 130 may be a low refractive index layer formed of a material having a lower refractive index than the substrate 100. The refractive index of such a low refractive index layer is preferably 1.20 to 1.55, more preferably 1.30 to 1.50. The thickness of the low refractive index layer is preferably 50 to 400 nm, more preferably 50 to 200 nm. The low refractive index layer may be a layer made of a fluoropolymer with a low refractive index, a layer formed by a sol-gel process, or a layer containing particles.

The layer containing particles has microvoids between the particles or in the particles. The porosity of the layer containing particles is preferably 3% to 50% by volume, more preferably 5% to 35% by volume.

The antireflective layer 130 can be formed of a laminate of one or more low refractive index sublayers and one or more medium or high refractive index sublayers to prevent reflection of light of broader wavelength range. The refractive index of a high refractive index sublayer is preferably 1.65 to 2.40, more preferably 1.70 to 2.20. The refractive index of a medium refractive sublayer is set to be the intermediate between the refractive indices of the low and the high refractive sublayers and preferably ranges from 1.50 to 1.90, more preferably 1.55 to 1.70. The thickness of the medium or high refractive index sublayer is preferably 5 nm to 100 μm, more preferably 10 nm to 10 μm, even more preferably 30 nm to 1 μm. The medium or high refractive index sublayer preferably has a haze of 5% or less, more preferably 3% or less, even more preferably 1% or less, unless it is functionalized for antiglare.

The medium and the high refractive index sublayers are formed by using polymer binders having relatively high refractive indices, such as polystyrene, styrene copolymers, polycarbonates, melamine resins, phenol resins, epoxy resins, and polyurethanes obtained by the reaction between a cyclic (alicyclic or aromatic) isocyanate and a polyol. Polymers having a cyclic (aromatic, heterocyclic or alicyclic) group and polymers having a halogen atom except fluorine as a substituent also have high refractive indices. Polymers may be formed from monomers having a double bond introduced therein and thereby capable of radical polymerization.

Fine inorganic particles may be dispersed in the above recited polymer binders to increase the refractive index. Inorganic particles having a refractive index of 1.80 to 2.80 are used preferably. Such inorganic particles are preferably prepared from metal oxides or sulfides, such as titanium oxide (including rutile, rutile/anatase mixed crystals, anatase, and amorphous oxide), tin oxide, indium oxide, zinc oxide, zirconium oxide, and zinc sulfide. Preferred of them are titanium oxide, tin oxide, and indium oxide. The inorganic particles may contain the metal oxide or sulfide as a major component and other elements. The term "major component" means a component present in the particles at the highest weight percentage. Other elements that may be present include Ti, Zr, Sn, Sb, Cu, Fe, Mn, Pb, Cd, As, Cr, Hg, Zn, Al, Mg, Si, P, and S. The medium or high refractive index sublayer can also be formed by using inorganic materials that are dispersible in a solvent or liquid per se and are capable of forming a film, such as alkoxides of various elements, salts of organic acids, coordination compounds having a coordinating compound bonded (e.g., chelate compounds), and inorganic active polymers.

The surface of the antireflective layer 130 may be endowed with an antiglare function for scattering incident light thereby preventing the surrounding environment from reflecting on the antireflective layer. An antiglare function can be imparted to the antireflective layer 130 by, for example, finely texturing the surface on which the antireflective layer 130 is to be formed (e.g., the surface of the primer layer 110) or embossing or otherwise roughening the surface of the antireflective layer 130. The antireflective layer functionalized for antiglare usually has a haze of 3% to 30%.

The hardcoat layer 140 is provided to protect the underlying layer(s) (i.e., the optically functional layer 120 and/or the antireflective layer 130) and formed of a material having higher hardness than the substrate 100. The hardcoat layer 140 preferably contains a crosslinked polymer. The hardcoat layer 140 can be formed using acrylic, urethane or epoxy polymers, oligomers or monomers, such as UV curing resins. The hardcoat layer 140 can also be made of a silica-based material. The thickness of the hardcoat layer 140 is preferably 0.1 to 100 μm, more preferably 1 to 30 μm.

The lubricating layer 150 may be provided on the surface of the light absorbing filter of the invention. The lubricating layer 150 imparts slip properties to the surface of the light absorbing filter thereby improving scratch resistance. The lubricating layer 150 can be formed using an organopolysiloxane (e.g., silicone oil), a natural wax, a petroleum wax, a higher fatty acid metal salt, or a fluorine-containing lubricant, or a derivative thereof. The lubricating layer 150 preferably has a thickness of 2 to 20 nm.

The primer layer 110, the antireflective layer 130, the hardcoat layer 140, and the lubricating layer 150 may be formed by any wet processes known in the art, such as dip coating, air knife coating, curtain coating, roller coating, wire bar coating, gravure coating, and extrusion coating. When the hardcoat layer 140 is formed from a silica-based material, it may be formed by any film formation techniques known in the art, such as evaporation deposition, sputtering, CVD, and laser ablation.

The layers composing the light absorbing filter of the invention may be formed sequentially, or two or more of them may be formed simultaneously.

Figure 2:
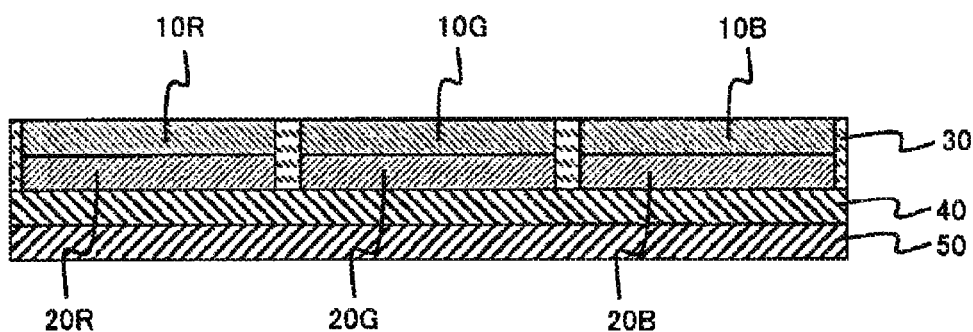
FIG. 2 is a schematic cross-section of a preferred embodiment of a color-converting light-emitting device according to the invention.

The color-converting light-emitting device according to the invention is not particularly limited as long as it includes a light emitting portion (light source) and, as a color conversion portion, the color conversion layer or color conversion filter of the invention. Otherwise, it is identical to conventional color converting light emitting devices. A preferred embodiment of the color converting light emitting device for, for instance, color display is illustrated in FIG. 2. The color converting light emitting device of FIG. 2 includes a substrate 50 and a light emitting layer 40 on the substrate 50. The means for causing the light emitting layer 40 to emit light is not particularly limited. For example, a light emitting layer of an electro luminescent (EL) device is caused to emit light by applying an electric current between electrodes having the light emitting layer therebetween.

A red color-conversion layer 20R, a green color-conversion layer 20G, and a blue color-conversion layer 20B are provided on the light emitting layer 40 to convert the color of the light emitted from the light emitting layer 40. At least one of these color conversion layers is the color conversion layer or color conversion filter of the present invention. The color conversion layer or the color conversion filter may be the red, green, or blue color-conversion layer 20R, 20G, or 20B according to the desired wavelength after conversion. The color conversion layer or filter may be a color conversion layer or filter using a film formed from a resin composition in which the Schiff base type compound of the invention is dissolved or dispersed in a binder resin.

If appropriate, a red, a green, and a blue color filter layer 10R, 10G, and 10B may be provided. These color filter layers are provided where it is required to optimize the chromatic coordinate or purity of the light converted through the red, green, or blue color conversion layer.

A black mask 30 is provided between the stacks of the red, green or blue color conversion layer 20R, 20G, or 20B and the red, green, or blue color filter layer 10R, 10G, or 10B. The black mask 30 is effective in increasing contrast.

The substrate 50 may be of an inorganic material such as glass or the polymer described. To facilitate forming electrodes that cause the light emitting layer 40 to emit light, a glass substrate is preferred.

The color filter layers 10R, 10B, and 10G have a function to transmit only light rays of desired wavelengths. The color filter layers 10R, 10B, and 10G are effective in blocking light rays from the light source that remain unconverted and improving the chromatic purity of the light rays having passed through the color conversion layers 20R, 20G, and 20B. The color filter layers may be formed of the materials of color filters for liquid crystal displays.

A color converting light emitting device for color display is composed of a plurality of sets of pixels arrayed in a matrix arrangement on a substrate 10, each set comprising the R, G, and B color-converting light emitting elements illustrated in FIG. 2. The pattern of arrangement of the color conversion filter layers depends on the intended use of the device. A red, a green, and a blue pixel having a rectangular, a circular, or any shape intermediate therebetween make one set, and the sets may be arranged in a matrix on the entire surface of the substrate 50. Or, color conversion layers of two different colors may be arranged in finely partitioned sections in an appropriate area ratio to display a monochromatic color that is not achieved with a color conversion layer of single color.

While FIG. 2 shows an embodiment in which a red, a green, and a blue color conversion layer are used, when a light emitting element that emits blue to green light is used as a light source, a color filter layer may be used alone without a color converting layer for blue. When the light from such a light source contains a sufficient amount of green region rays, light from the light source may be output only through a green color filter without using a color conversion layer for green.

Any light source that emits light in the near ultraviolet to visible region, preferably the near ultraviolet to bluish green region may be used as the light emitting portion. Examples of such a light source include an organic electro luminescent displays, a plasma light emitting device, a cold-cathode fluorescent lamp, a discharge lamp (e.g., a high pressure or ultra-high pressure mercury lamp or a xenon lamp), and an light emitting device.

When the color converting light emitting device of the invention has a color filter layer as illustrated in FIG. 2, the light emitting portion is disposed on the side of the color conversion layer.

When the color converting light emitting device of the invention has no color filter layer and uses, for example, the light absorbing filter shown in FIG. 1 (which contains no color filter layer) as a color conversion portion, the light emission portion may be disposed on either side of the light absorbing filter. When a color conversion layer itself is used as a color conversion portion, the conversion layer may be stacked directly on the surface of the light source.

Figure 3:
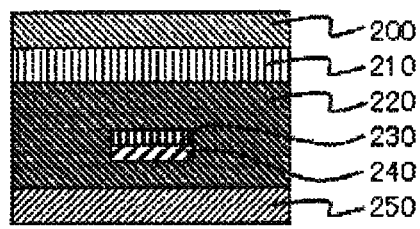
FIG. 3 is a schematic cross-section of a preferred embodiment of a photoelectric device according to the invention.

The photoelectric device according to the invention is not particularly limited as long as it includes a photoelectric element and the color conversion filter of the invention. Otherwise, it is identical to conventional color photoelectric devices. A solar cell as a preferred embodiment of the photoelectric device of the invention is illustrated in FIG. 3. In order for a photoelectric element 240 to generate electricity at high efficiency, the neighboring layers including a topsheet layer 200, a transparent substrate 210, a filler layer 220, a light collecting film 230, and a backsheet layer 250 can be made into a color conversion filter. That is, the effects of the invention are obtained by incorporating the Schiff base type compound of the invention into the element(s) near the photoelectric element. A color conversion layer may separately be provided to obtain the same effects. For example, a color conversion layer may be provided between layers using an adhesive containing the Schiff base type compound of the invention.

The photoelectric device of the invention is exemplified by, but not limited to, a solar cell, including a silicon solar cell, a compound solar cell, and an organic solar cell.

EXAMPLES

The present invention will now be illustrated in greater detail with reference to Preparation Examples, Examples, and Evaluation Examples, but it should be understood that the invention is not construed as being limited thereto.

Preparation Examples 1-1 to 1-12

Preparation of Compound Nos. 1 Through 9, 11, 55, and 56

In a reaction flask, 0.01 mol of each of the starting compounds shown in Table 1 or 2 and numbered 1 through 9, 11, 55, and 56 and 0.012 mol of diisopropylethylamine were dissolved in 12 g of dichloromethane. To the solution was added dropwise 0.012 mol of $BF_3/Et_2O$ under cooling in a water bath over a period of 10 minutes, and the mixture was stirred for the reaction time shown in Table 1 or 2. Twenty milliliters of water was added, and the stirring was continued for an additional 1 hour period. After oil-water separation, the oily phase was dried over $Na_2SO_4$, filtered, and concentrated. The residue was purified by column chromatography using chloroform as a developing solvent, and the column eluate was concentrated and dried in vacuo at 60° C. for 1 hour to give a Schiff base type compound (compound No. 1 through 9, 11, 55, or 56, respectively) of the invention having the appearance shown in Table 1 or 2 in the yield shown in Table 1 or 2. The resulting compounds were identified by $^1$H-NMR and mass spectrometry (MALDI-TOF-MS). The results of the identification are shown in Tables 3 and 4.

TABLE 1

| Desired Compound | | Starting Compound | Reaction Time | Appearance | Yield |
|---|---|---|---|---|---|
| Prepn. Example 1-1 | Compound No. 1 | 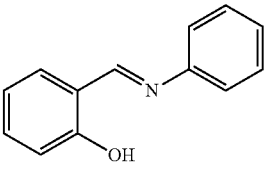<br>No. 1 | 1.5 h | pale yellow solid | 83% |
| Prepn. Example 1-2 | Compound No. 2 | 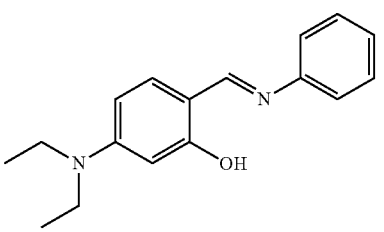<br>No. 2 | 4.5 h | pale yellow solid | 42% |
| Prepn. Example 1-3 | Compound No. 3 | 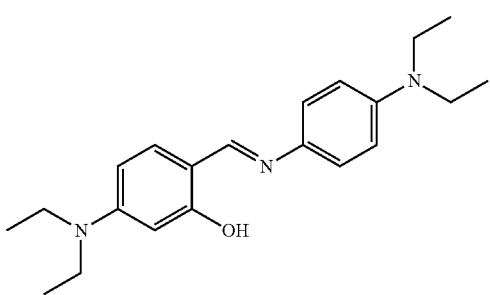<br>No. 3 | 2 h | orange solid | 54% |
| Prepn. Example 1-4 | Compound No. 4 | 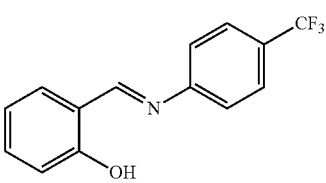<br>No. 4 | 2.5 h | white solid | 33% |

TABLE 1-continued
| Desired Compound | Starting Compound | Reaction Time | Appearance | Yield |
|---|---|---|---|---|
| Prepn. Example 1-5 Compound No. 5 | 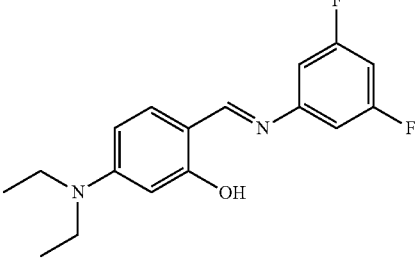<br>No. 5 | 2 h | pale yellow solid | 73% |
| Prepn. Example 1-6 Compound No. 6 | 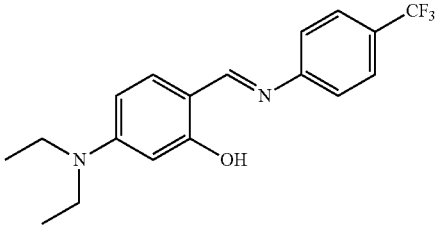<br>No. 6 | 5.5 h | yellow solid | 73% |
TABLE 2
| Desired Compound | Starting Compound | Reaction Time | Appearance | Yield |
|---|---|---|---|---|
| Prepn. Example 1-7 Compound No. 7 | 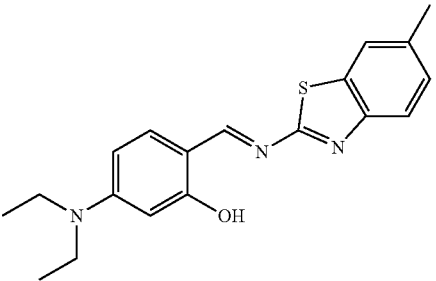<br>No. 7 | 15 h | orange solid | 45% |
| Prepn. Example 1-8 Compound No. 8 | 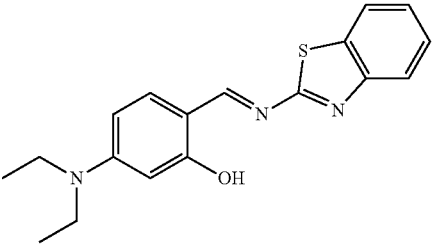<br>No. 8 | 3 h | orange solid | 65% |

TABLE 2-continued

| Desired Compound | | Starting Compound | Reaction Time | Appearance | Yield |
|---|---|---|---|---|---|
| Prepn. Example 1-9 | Compound No. 9 | No. 9 | 5 h | yellow solid | 82% |
| Prepn. Example 1-10 | Compound No. 11 | No. 11 | 2 h | pale yellow solid | 66% |
| Prepn. Example 1-11 | Compound No. 55 | No. 55 | 24 h | yellow solid | 61% |
| Prepn. Example 1-12 | Compound No. 56 | No. 56 | 7 h | yellow solid | 73% |

TABLE 3

$^1$H-NMR (CDCl$_3$)

Chemical Shift; ppm (multiplicity, number of protons)

Compound No. 1  7.04 (t, 1H), 7.17 (d, 1H), 7.44-7.56 (m, 6H), 7.67 (t, 1H), 8.44 (s, 1H)
Compound No. 2  1.24 (t, 6H), 3.45 (q, 4H), 6.24 (d, 1H), 6.35 (dd, 1H), 7.22 (d, 1H),
7.33 (t, 1H), 7.42 (t, 2H), 7.49 (d, 2H), 8.03 (s, 1H)
Compound No. 3  1.14-1.24 (m, 12H), 3.33-3.46 (m, 8H), 6.24 (d, 1H), 6.32 (dd, 1H),
6.65 (d, 2H), 7.18 (d, 1H), 7.34 (d, 2H), 7.98 (s, 1H)
Compound No. 4  7.07 (t, 1H), 7.18 (d, 1H), 7.53 (dd, 1H), 7.68-7.80 (m, 5H), 8.47 (s, 1H)
Compound No. 5  1.25 (t, 6H), 3.46 (q, 4H), 6.21 (d, 1H), 6.38 (dd, 1H), 6.77 (tt, 1H),
7.08 (d, 2H), 7.23 (d, 1H), 8.01 (s, 1H)
Compound No. 6  1.25 (t, 6H), 3.46 (q, 4H), 6.22 (d, 1H), 6.37 (dd, 1H), 7.23 (d, 1H),
7.61 (d, 2H), 7.67 (d, 2H), 8.04 (s, 1H)
Compound No. 7  1.27 (t, 6H), 2.48 (s, 3H), 3.49 (q, 4H), 6.21 (d, 1H), 6.43 (dd, 1H),
7.26 (d, 1H), 7.33 (d, 1H), 7.61 (s, 1H), 7.75 (d, 1H), 9.12 (s, 1H)
Compound No. 8  1.27 (t, 6H), 3.49 (q, 4H), 6.20 (d, 1H), 6.44 (dd, 1H), 7.31-7.36 (m, 2H),
7.46 (t, 1H), 7.82 (d, 1H), 7.87 (d, 1H), 9.15 (s, 1H)
Compound No. 9  1.19 (t, 6H), 3.39 (q, 4H), 6.68 (d, 2H), 7.00 (t, 1H), 7.13 (d, 1H),
7.40-7.46 (m, 3H), 7.58 (t, 1H), 8.34 (s, 1H)
Compound No. 11  1.35 (s, 9H), 1.57 (s, 9H), 7.82 (d, 1H), 8.04-8.18 (m, 6H),
8.20-8.28 (m, 3H), 8.48 (s, 1H)
Compound No. 55  8.11 (d, 1H), 8.08 (d, 1H), 7.99 (s, 1H), 7.61 (d, 1H), 7.47 (t, 1H),
7.40-7.37 (m, 2H), 7.25-7.20 (m, 1H), 6.80 (s, 1H), 4.35 (q, 2H),
3.33-3.29 (m, 4H), 2.83 (t, 2H), 2.67 (t, 3H), 1.94-1.91 (m, 4H),
1.42 (t, 3H)
Compound No. 56  8.01 (s, 1H), 7.35 (d, 2H), 7.28-7.23 (m, 4H), 7.18 (d, 1H),
7.11-7.01 (m, 8H), 6.32 (d, 1H), 6.21 (s, 1H), 3.35 (t, 4H),
1.66-1.55 (m, 4H), 1.41-1.31 (m, 4H), 0.97 (t, 6H)

TABLE 4

| Mass Spectrometry (MALDI-TOF-MS) | | |
|---|---|---|
| | Calculated | Found Value |
| Compound No. 1 | 245.04 | 246.2[M+] |
| Compound No. 2 | 316.16 | 317.3[M+] |
| Compound No. 3 | 387.28 | 387.4[M+] |
| Compound No. 4 | 313.04 | 314.2[M+] |
| Compound No. 5 | 352.14 | 353.3[M+] |
| Compound No. 6 | 384.16 | 384.0[M−] |
| Compound No. 7 | 387.26 | 388.3[M+] |
| Compound No. 8 | 373.24 | 374.3[M+] |
| Compound No. 9 | 316.16 | 317.3[M+] |
| Compound No. 11 | 481.40 | 481.5[M+] |
| Compound No. 55 | 457.34 | 457.3[M+] |
| Compound No. 56 | 539.48 | 539.5[M+] |

[chem. 10]

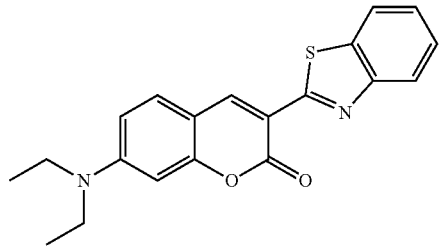

Comparative compound No. 1

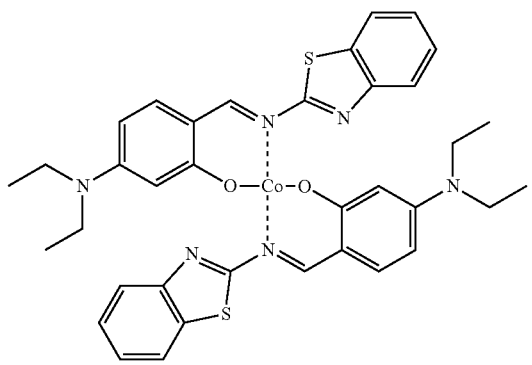

Comparative compound No. 2

Examples 1-1 to 1-12 and Comparative Examples 1-1 to 1-3

Fluorescence spectra of Schiff base type compound Nos. 1 to 9, 11, 55, and 56 obtained in Preparation Examples 1-1 to 1-12 and comparative compounds I to 3 shown [Chem.10] below were determined in a toluene solvent using a spectrophotometer U-3010 (for absorption spectrometry) and a fluorescence spectrophotometer F4500 (for fluorescence spectrometry), both from Hitachi High-Technologies Corp. The results of fluorescence spectrophotometry are shown in Table 5.

-continued

Comparative compound No. 3

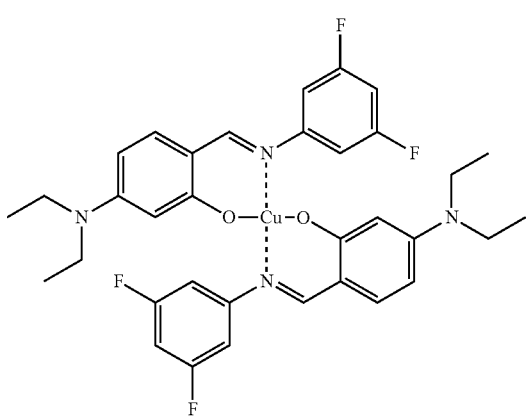

TABLE 5

| | Schiff Base Compound | $\lambda_{max}$ (nm) | $\epsilon$ (M$^{-1}$cm$^{-1}$) | Fluorescence Maximum (nm) | Fluorescence Intensity | Density (M) |
|---|---|---|---|---|---|---|
| Example 1-1 | Compound No. 1 | 365 | 8.60 ×10$^3$ | 465.4 | 24.2 | 3.72 × 10$^{-5}$ |
| Example 1-2 | Compound No. 2 | 395 | 5.17 × 10$^4$ | 446.4 | 43.8 | 7.21 × 10$^{-6}$ |
| Example 1-3 | Compound No. 3 | 421 | 3.88 × 10$^4$ | 557.8 | 21.2 | 1.14 × 10$^{-5}$ |
| Example 1-4 | Compound No. 4 | 375 | 8.11 × 10$^3$ | 478.2 | 76.6 | 6.08 × 10$^{-5}$ |
| Example 1-5 | Compound No. 5 | 406 | 5.60 × 10$^4$ | 451.6 | 283.3 | 6.59 × 10$^{-6}$ |
| Example 1-6 | Compound No. 6 | 405 | 5.52 × 10$^4$ | 451.4 | 402.8 | 6.56 × 10$^{-6}$ |
| Example 1-7 | Compound No. 7 | 446 | 6.87 × 10$^4$ | 526.2 | 202.7 | 5.58 × 10$^{-6}$ |
| Example 1-8 | Compound No. 8 | 443 | 6.98 × 10$^4$ | 485.8 | 467.6 | 7.01 × 10$^{-6}$ |
| Example 1-9 | Compound No. 9 | 421 | 1.65 × 10$^4$ | 556.8 | 68.0 | 3.72 × 10$^{-5}$ |
| Example 1-10 | Compound No. 11 | 388 | 1.04 × 10$^4$ | 548.0 | 58.1 | 4.18 × 10$^{-5}$ |
| Example 1-11 | Compound No. 55 | 418 | 5.09 × 10$^4$ | 495.0 / 520.2 | 48.9 / 48.4 | 1.19 × 10$^{-5}$ |
| Example 1-12 | Compound No. 56 | 420 | 4.50 × 10$^4$ | 555 | 70.3 | 1.05 × 10$^{-5}$ |
| Comp. Example 1-1 | Comp. Compound No. 1 | 438 | 5.07 × 10$^4$ | 480.4 | 619.8 | 6.56 × 10$^{-6}$ |
| Comp. Example 1-2 | Comp. Compound No. 2 | 433 | 5.65 × 10$^4$ | undetected | undetected | 5.88 × 10$^{-6}$ |
| Comp. Example 1-3 | Comp. Compound No. 3 | 375 | 7.22 × 10$^4$ | undetected | undetected | 6.21 × 10$^{-6}$ |

Examples 2-1 to 2-6 and Comparative Example 2-1

The quantum efficiency of the Schiff base type compounds shown in Table 5 and comparative compound I, all in powder form, was determined using a fluorescence spectrophotometer F4500 from Hitachi High-Technologies Corp. and a φ60 integrating sphere. Light having a wavelength near the absorption maximum wavelength ($\lambda_{max}$) in a toluene solvent was used as exciting light. The quantum efficiency was calculated from the area ratio. The results are shown in Table 6.

TABLE 6

| | Schiff Base Compound | Quantum Efficiency (%) |
|---|---|---|
| Example 2-1 | Compound No. 2 | 49.9 |
| Example 2-2 | Compound No. 3 | 58.4 |
| Example 2-3 | Compound No. 5 | 57.6 |
| Example 2-4 | Compound No. 6 | 39.5 |
| Example 2-5 | Compound No. 7 | 11 |
| Example 2-6 | Compound No. 8 | 24.4 |
| Comp. Example 2-1 | Comp. Compound 1 | 4.4 |

It is apparent from Table 6 that the Schiff base type compounds of the invention emit high fluorescence in their solid state as well.

Examples 3-1 to 3-6 and Comparative Example 3-1

Each of the Schiff base type compounds and comparative compound shown in Table 7 was dissolved in a 20 wt % solution of polymethyl methacrylate in toluene in a concentration showing an absorbance of 0.5 at the $\lambda_{max}$. The solution was applied to a 100 μm thick polyethylene terephthalate film with a wire bar RDS30 (from RDS Webster, N.Y.) and heated in an oven at 100° C. for 10 minutes to obtain an optical filter (color conversion filter) of the invention or for comparison. The absorption spectrum of the resulting optical filter was determined using a spectrophotometer U-3010 from Hitachi High-Technologies Corp. The fluorescence spectrum was then determined using a fluorescence spectrophotometer F4500 from Hitachi High-Technologies Corp. Light having a wavelength of the $\lambda_{max}$ of each individual filter was used as exciting light. The quantum efficiency of the filter was determined using a fluorescence spectrophotometer F4500 from Hitachi High-Technologies Corp. and a φ60 integrating sphere. Light having a wavelength near the $\lambda_{max}$ of each individual filter was used as exciting light. The quantum efficiency was calculated from the area ratio. The results are shown in Table 7.

TABLE 7

| Optical Filter | Schiff Base Compound | $\lambda_{max(nm)}$ | Abs. | $EM_{max}$ (nm) | Fluorescence Intensity | Quantum Efficiency (%) |
|---|---|---|---|---|---|---|
| Example 3-1 | Compound No. 2 | 398 | 0.52 | 448.2 | 489.2 | 56.7 |
| Example 3-2 | Compound No. 3 | 417 | 0.52 | 542.2 | 209.9 | 53.2 |
| Example 3-3 | Compound No. 5 | 408 | 0.52 | 455.6 | 468.9 | 51.4 |
| Example 3-4 | Compound No. 6 | 406 | 0.49 | 455.4 | 486.1 | 57.0 |
| Example 3-5 | Compound No. 7 | 446 | 0.48 | 521.0 | 311.0 | 49.4 |
| Example 3-6 | Compound No. 8 | 443 | 0.54 | 488.2 | 395.8 | 45.2 |
| Comp. Example 3-1 | Comp. Compound 1 | 448 | 0.58 | 495.8 | 519.6 | 35.1 |

It is apparent from Table 7 that the Schiff base type compounds of the invention emit high fluorescence in the form of film as well.

Evaluation Examples 1-1 to 1-6 and Comparative Evaluation Example 1-1

The optical filters of the invention obtained in Examples 3-1 to 3-6 and the comparative optical filter obtained in Comparative Example 3-1 were evaluated for light resistance (24-hour irradiation) using a xenon Weather-O-Meter Table Sun from Suga Test Instruments Co., Ltd. The fluorescence intensity of the filter was measured at the emission maximum wavelength ($EM_{max}$) of each individual filter before and after 24-hour irradiation. The fluorescence intensity after the irradiation was relatively expressed with the initial value (before irradiation) taken as 100. The results obtained are shown in Table 8.

TABLE 8

| | Optical Filter | Fluorescence Intensity after 24 hr Irradiation |
|---|---|---|
| Evaluation Example 1-1 | Example 2-1 | 18 |
| Evaluation Example 1-2 | Example 2-2 | 34 |
| Evaluation Example 1-3 | Example 2-3 | 35 |
| Evaluation Example 1-4 | Example 2-4 | 36 |
| Evaluation Example 1-5 | Example 2-5 | 49 |
| Evaluation Example 1-6 | Example 2-6 | 46 |
| Comp. Evaluation Example 1-1 | Comp. Example 2-1 | 10 |

It is apparent from Table 8 that the optical filter containing a compound structurally different from the compounds of the invention undergoes great reduction in fluorescence intensity when irradiated with xenon light, whilst the optical filters containing the Schiff base type compound of the invention are superior in light resistance.

As described, it has been demonstrated that the Schiff base type compound of the invention emits fluorescence in any of solution, solid, and film forms and that the optical filter (color conversion filter) containing the Schiff base type compound of the invention is excellent in color conversion performance and light resistance and therefore useful in color converting light emitting devices and photoelectric devices.

10R: red filter layer
10G: green filter layer
10B: blue filter layer
20R: red color-conversion layer
20G: green color-conversion layer
20B: blue color-conversion layer
30: black mask
40: light emitting layer
50: substrate
100: substrate
105: optically functional substrate
110: primer layer
120: optically functional layer
130: antireflective layer
140: hardcoat layer
150: lubricating layer
200: topsheet layer
210: transparent substrate
220: filler layer
230: light collecting film
240: photoelectric element
250: backsheet layer

The invention claimed is:
1. A color conversion layer, comprising a coloring material comprising:
at least one Schiff base type compound represented by general formula (I):

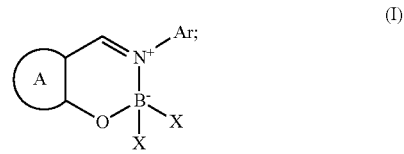

and
a binder resin,
wherein
ring A represents an aromatic ring, an aliphatic ring, or a heterocyclic ring;
Ar represents a 5- or 6-membered heterocyclic or aromatic ring; and
X represents a halogen atom,
the aliphatic ring represented by ring A and the aromatic ring and the heterocyclic ring represented by ring A or Ar being optionally fused to a ring or optionally substituted, and
rings A and Ar are unsubstituted, or at least one of the hydrogen atoms bonded to ring A or Ar is substituted by an alkyl group, an alkoxy group, an alkylthio group, an alkenyl group, an arylalkylgroup, an aryl group, an aryloxy group, an arylthio group, a heterocyclic group, a halogen atom, an acyl group, an acyloxy group, a sulfonamide group, a sulfonyl group, a carboxyl group, a cyano group, a sulfo group, a hydroxyl group, a nitro group, a mercapto group, an imido group, or a carbamoyl group.
2. The color conversion layer according to claim 1, wherein the Schiff base type compound is represented by general formula (II):

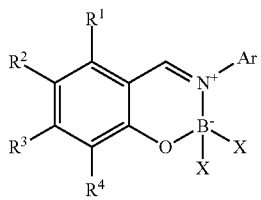
(II)

wherein
$R^1$, $R^2$, $R^3$, and $R^4$ each independently represent a hydrogen atom, a halogen atom, a nitro group, a cyano group, a hydroxyl group, a carboxyl group, —NRR', an optionally substituted alkyl group having 1 to 20 carbon atoms, an optionally substituted aryl group having 6 to 20 carbon atoms, an optionally substituted heterocyclic ring having 4 to 20 carbon atoms, or an optionally substituted arylalkyl group having 7 to 20 carbon atoms; or adjacent two of $R^1$, $R^2$, $R^3$, and $R^4$ are taken together to form an aliphatic, aromatic, or heterocyclic ring, a methylene chain of the alkyl group or the arylalkyl group and the bond between the aryl group and the benzene ring being optionally interrupted by —O—, —S—, —SO$_2$—, —CO—, —OCO—, or —COO—; and R and R' each represent an alkyl group having 1 to 20 carbon atoms or an aryl group having 6 to 20 carbon atoms; or R and R' are taken together with the adjacent $R^1$, $R^2$, $R^3$, or $R^4$ to form a ring structure, the aromatic ring formed by the connection of adjacent two of $R^1$, $R^2$, $R^3$, and $R^4$ being optionally fused to a ring or substituted;

Ar and X are as defined for general formula (I); and $R^1$, $R^2$, $R^3$, and $R^4$ each represents a hydrogen atom and Ar is unsubstituted, or $R^1$, $R^2$, $R^3$, or $R^4$, or at least one of the hydrogen atoms bonded to Ar is displaced by an alkyl group, an alkoxy group, an alkylthio group, an alkenyl group, an arylalkyl group, an aryl group, an aryloxy group, an arylthio group, a heterocyclic group, a halogen atom, an acyl group, an acyloxy group, a sulfonamide group, a sulfonyl group, a carboxyl group, a cyano group, a sulfo group, a hydroxyl group, a nitro group, a mercapto group, an imido group, or a carbamoyl group.

3. The color conversion layer according to claim 2, wherein the Schiff base type compound is represented by general formula (III):

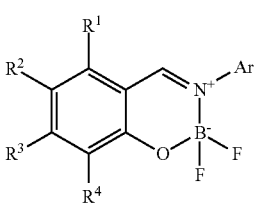
(III)

wherein
Ar is as defined for general formula (I); and
$R^1$, $R^2$, $R^3$, and $R^4$ are as defined for general formula (II).

4. A color conversion filter comprising one or more color conversion layers, at least one of said layers being the color conversion layer according to claim 1.

5. A light absorbing layer, comprising a coloring material comprising:

at least one Schiff base type compound represented by general formula (I):

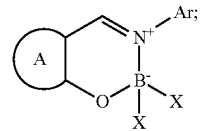
(I)

and
a binder resin,
wherein
ring A represents an aromatic ring, an aliphatic ring, or a heterocyclic ring;
Ar represents a 5- or 6-membered heterocyclic or aromatic ring; and
X represents a halogen atom,
the aliphatic ring represented by ring A and the aromatic ring and the heterocyclic ring represented by ring A or Ar being optionally fused to a ring or optionally substituted, and
rings A and Ar are unsubstituted, or at least one of the hydrogen atoms bonded to ring A or Ar is substituted by an alkyl group, an alkoxy group, an alkylthio group, an alkenyl group, an arylalkyl group, an aryl group, an aryloxy group, an arylthio group, a heterocyclic group, a halogen atom, an acyl group, an acyloxy group, a sulfonamide group, a sulfonyl group, a carboxyl group, a cyano group, a sulfo group, a hydroxyl group, a nitro group, a mercapto group, an imido group, or a carbamoyl group.

6. The light absorbing layer according to claim 5, wherein the Schiff base type compound is represented by general formula (II):

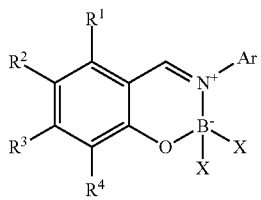
(II)

wherein
$R^1$, $R^2$, $R^3$, and $R^4$ each independently represent a hydrogen atom, a halogen atom, a nitro group, a cyano group, a hydroxyl group, a carboxyl group, —NRR', an optionally substituted alkyl group having 1 to 20 carbon atoms, an optionally substituted aryl group having 6 to 20 carbon atoms, an optionally substituted heterocyclic ring having 4 to 20 carbon atoms, or an optionally substituted arylalkyl group having 7 to 20 carbon atoms; or adjacent two of $R^1$, $R^2$, $R^3$, and $R^4$ are taken together to form an aliphatic, aromatic, or heterocyclic ring, a methylene chain of the alkyl group or the arylalkyl group and the bond between the aryl group and the benzene ring being optionally interrupted by —O—, —S—, —SO$_2$—, —CO—, —OCO—, or —COO—; and R and R' each represent an alkyl group having 1 to 20 carbon atoms or an aryl group having 6 to 20 carbon atoms; or R and R' are taken together with the adjacent $R^1$, $R^2$, $R^3$, or $R^4$ to form a ring structure, the aromatic ring formed by the connection of adjacent two of $R^1$, $R^2$, $R^3$, and $R^4$ being optionally fused to a ring or substituted; Ar and X are as defined for general formula (I); and $R^1$, $R^2$, $R^3$, and $R^4$ each represents a hydrogen atom and Ar is unsubstituted, or $R^1$, $R^2$, $R^3$, or $R^4$, or at least one of the hydrogen atoms bonded to Ar is displaced by an alkyl group, an alkoxy group, an alkylthio group, an alkenyl group, an arylalkylgroup, an aryl group, an aryloxy group, an arylthio group, a heterocyclic group, a halogen atom, an acyl group, an acyloxy group, a sulfonamide group, a sulfonyl group, a carboxyl group, a cyano group, a sulfo group, a hydroxyl group, a nitro group, a mercapto group, an imido group, or a carbamoyl group.

7. The light absorbing layer according to claim 6, wherein the Schiff base type compound is represented by general formula (III):

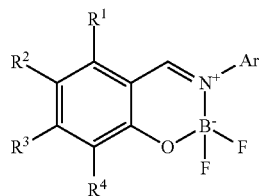
(III)

wherein
Ar is as defined for general formula (I); and
$R^1$, $R^2$, $R^3$, and $R^4$ are as defined for general formula (II).

8. A light absorbing filter comprising one or more light absorbing layers, at least one of said layers being the light absorbing layer according to claim 5.

* * * * *